United States Patent [19]
Waxman et al.

[11] Patent Number: 5,968,010
[45] Date of Patent: Oct. 19, 1999

[54] METHOD FOR TRANSVENOUSLY ACCESSING THE PERICARDIAL SPACE VIA THE RIGHT ATRIUM

[75] Inventors: Sergio Waxman, Brighton; Richard L. Verrier, Wellesley Hills, both of Mass.

[73] Assignee: Beth Israel Deaconess Medical Center, Inc., Boston, Mass.

[21] Appl. No.: 08/841,344

[22] Filed: Apr. 30, 1997

[51] Int. Cl.[6] .................................................. A61M 31/00
[52] U.S. Cl. ............................................................ 604/49
[58] Field of Search .............................. 604/280, 49, 264, 604/96, 164, 50–53

[56] References Cited

U.S. PATENT DOCUMENTS

| | | | |
|---|---|---|---|
| 3,630,207 | 12/1971 | Kahn et al. | 128/350 R |
| 3,680,544 | 8/1972 | Shinnick et al. | 128/2 R |
| 4,003,379 | 1/1977 | Ellinwood, Jr. | 128/260 |
| 4,146,029 | 3/1979 | Ellinwood, Jr. | 128/260 |
| 4,173,981 | 11/1979 | Mortensen | 128/348 |
| 4,181,123 | 1/1980 | Crosby | 128/6 |
| 4,256,115 | 3/1981 | Bilitch | 128/419 P |
| 4,292,976 | 10/1981 | Banka | 128/656 |
| 4,296,100 | 10/1981 | Franco | 424/108 |
| 4,319,562 | 3/1982 | Crosby | 128/1 R |
| 4,567,900 | 2/1986 | Moore | 128/784 |
| 4,619,247 | 10/1986 | Inoue et al. | 128/6 |
| 4,699,147 | 10/1987 | Chilson et al. | 128/642 |
| 4,708,145 | 11/1987 | Tacker, Jr. et al. | 128/419 D |
| 4,717,387 | 1/1988 | Inoue et al. | 604/264 |
| 4,765,341 | 8/1988 | Mower et al. | 128/785 |
| 4,769,016 | 9/1988 | Labianca | 604/280 |
| 4,865,037 | 9/1989 | Chin et al. | 128/419 D |
| 4,884,567 | 12/1989 | Elliott et al. | 128/303 R |
| 4,946,457 | 8/1990 | Elliott | 606/1 |
| 4,961,731 | 10/1990 | Bodicky et al. | 604/264 |
| 4,991,578 | 2/1991 | Cohen . | |
| 4,991,603 | 2/1991 | Cohen et al. | 128/786 |
| 4,998,975 | 3/1991 | Cohen et al. | 128/419 D |
| 5,033,477 | 7/1991 | Chin et al. | 128/785 |
| 5,092,848 | 3/1992 | deCiutiis | 604/170 |
| 5,137,510 | 8/1992 | VanDeripe | 604/28 |
| 5,147,336 | 9/1992 | Wendell et al. | 604/283 |
| 5,269,326 | 12/1993 | Verrier | 128/642 |
| 5,713,849 | 2/1998 | Bosma et al. | 604/28 |
| 5,722,972 | 3/1998 | Power et al. | 606/7 |
| 5,725,512 | 3/1998 | Swartz et al. | 604/280 |

OTHER PUBLICATIONS

DiCarlo, S.E. et al., "Exercise training enhances cardiac afferent inhibitions of baroreflex function", *The American Physiological Society*, Order No. 0363–6135, 1990, pp. H212–H220.

Dorward, P.K. et al., "Blockade Of Cardiac Nerves By Intrapericardial Local Anaesthetics In The Conscious Rabbit", *Aust. J. Exp. Biol. Med. Sci.*, vol. 61 (Pt. 2), 1983, pp. 219–230.

Miyazaki, T. et al., "Presynaptic Modulation of Efferent Sympathetic and Vagal Neurotransmission in the Canine Heart by Hypoxia, High $K^+$, Low pH, and Adenosine", *Circulation Research*, vol. 66, No. 2, Feb., 1990, pp. 289–301.

(List continued on next page.)

*Primary Examiner*—Manuel Mendel
*Attorney, Agent, or Firm*—Sterne-Kessler-Goldstein & Fox P.L.L.C.

[57] ABSTRACT

A method for placing various types of catheters into the pericardial space takes advantage of the fact that the right auricle is a thin-walled, low-pressure structure which can be readily penetrated without damaging the pericardium or the epicardium. A guide catheter is passed through a selected peripheral vein to establish a transvenous route to the right auricle of the heart. A needle catheter is then passed through the guide catheter and into the right auricle so that a distal end of the needle catheter is positioned against a wall of the right auricle. The wall of the right auricle is then pierced with the needle catheter. A guide wire is advanced through the needle catheter and into the pericardial space. Once in position, the guide wire can be used as a conduit over which a desired catheter may be introduced for performing a specific medical procedure.

23 Claims, 7 Drawing Sheets

OTHER PUBLICATIONS

Miyazaki, T. et al., "Prostaglandins in the Pericardial Fluid Modulate Neural Regulation of Cardiac Electrophysiological Properties", *Circulation Research*, vol. 66, No. 1, Jan., 1990, pp. 163–175.

Avitall, B. et al., "Iontophoretic Delivery of Dobutamine: An Effective Method To Increase Contractility of Non–Transmural Infarcts", *JACC*, vol. 17, No. 2, Feb., 1991, p. 27A. (Abstract only).

Avitall, B. et al., "Iontophoretic Transport of Procainamide and D–Sotalol Into Arrhythmogenic Myocardium: Efficacy in Vertricular Tachycardia Suppression", *JACC*, vol. 17, No. 2, Feb., 1991, p. 39A. (Abstract only).

Avitall, B. et al., "A New Technique For AV Nodal Modification Using Perinodal Injection Of A Sclerosing Agent", *JACC*, vol. 17, No. 2, Feb., 1991, p. 174A. (Abstract only).

Verrier, R.L. et al., "Prevention Of Ventricular Fibrillation By Use Of Low–Intensity Electrical Stimuli", Reprinted from *the Annals of the New York Academy of Sciences*, 1982, pp. 355–370.

Verrier, R.L. et al., "Protective zone and the determination of vulnerability to ventricular fibrillation", *The American Physiology Society*, 1978, Order No. 0363–6135/78/0000–0000, pp. H592–H596.

Buselmeier, T.J. et al., "Treatment of Intractable Uremic Pericardial Effusion: Avoidance of Pericardiectomy With Local Steroid Instillation", *Journal of the American Medical Association*, vol. 240, No. 13, 1978, pp. 1358–1359.

Baim et al., *Cardiac Catheterization, Angiography, and Intervention*, Fifth Edition, Williams and Wilkins Publishing, 1996, pp. 809–811 and 813.

Brockenbrough et al., "A New Technic for Left Ventricular Angiocardiography and Transseptal Left Heart Catheterization," *The American Journal of Cardiology*, Dec., 1960, pp. 1062–1064.

Uchida et al., "Angiogenic Therapy of Acute Myocardial Infarction by Intrapericardial Injection of Basic Fibroblast Growth Factor and Heparin Sulfate: An Experimental Study," *American Heart Journal*, vol. 130, No. 6, Dec., 1995, pp. 1182–1188.

Welt et al., "Second International Symposium on Cardiovascular Drug Delivery," *Circulation*, vol. 95, No. 4, Feb. 18, 1997, pp. 773–776.

202

```
┌─────────────────────────────────────────────┐
│  SELECT A PERIPHERAL VEIN AS AN ACCESS SITE │─── 302
└─────────────────────────────────────────────┘
                      ↓
┌─────────────────────────────────────────────┐
│  PLACE AN INTRODUCER SHEATH IN SAID VEIN TO │
│  PROTECT THE PERIPHERAL VEIN AND FACILITATE │─── 304
│     INTRODUCTION OF VARIOUS CATHETERS       │
└─────────────────────────────────────────────┘
                      ↓
┌─────────────────────────────────────────────┐
│ USE A GUIDE CATHETER TO ESTABLISH A TRANSVENOUS │─── 306
│   ROUTE TO THE RIGHT AURICLE OF THE HEART   │
└─────────────────────────────────────────────┘
                      ↓
┌─────────────────────────────────────────────┐
│  PASS A NEEDLE CATHETER THROUGH THE GUIDE CATHETER │
│  AND INTO THE RIGHT AURICLE SO THAT A DISTAL END OF│─── 308
│  THE NEEDLE CATHETER IS AGAINST THE WALL OF THE RIGHT│
│                    AURICLE                  │
└─────────────────────────────────────────────┘
                      ↓
┌─────────────────────────────────────────────┐
│  PIERCE THE WALL OF THE RIGHT AURICLE WITH  │─── 310
│            THE NEEDLE CATHETER              │
└─────────────────────────────────────────────┘
                      ↓
┌─────────────────────────────────────────────┐
│ ADVANCE A GUIDE WIRE THROUGH THE NEEDLE CATHETER │─── 312
│      AND INTO THE PERICARDIAL SPACE         │
└─────────────────────────────────────────────┘
                      ↓
┌─────────────────────────────────────────────┐
│ USE FLUOROSCOPIC IMAGING TO CONFIRM POSITIONING OF │─── 314
│  THE GUIDE WIRE WITHIN THE PERICARDIAL SPACE│
└─────────────────────────────────────────────┘
```

FIG. 3

METHOD FOR TRANSVENOUSLY ACCESSING THE PERICARDIAL SPACE VIA THE RIGHT ATRIUM

BACKGROUND OF THE INVENTION

1. Field of the Invention

The invention relates to the field of cardiology. More specifically, the invention relates to a method for diagnosing and treating the heart by facilitating access to the pericardial space.

2. Background Art

An important problem in cardiology is the provision of a safe method for diagnosing and treating the heart selectively and without thoracotomy (open chest surgery). Diagnosis or treatment may be pharmacologic or electrophysiologic. For example, in order to deliver electrical stimuli directly to the heart for the purpose of cardioversion or defibrillation, patients often undergo a thoracotomy under general anesthesia for attachment of a "patch" electrode to the epicardial surface. This procedure requires an extensive incision of the pericardium. The "patch" electrode provides a large electrode surface area in contact with the heart so that a sufficient mass of cardiac tissue may be depolarized. Thoracotomy creates the additional complication of wound healing.

It is desirable to provide a method for placing the defibrillation/cardioversion electrodes in contact with the heart muscle without thoracotomy. U.S. Pat. Nos. 4,181,562 and 4,319,562 to Crosby, and 5,033,477 to Chin et al. disclose methods for placing electrodes in contact with the heart muscles from within the pericardial space without the need for thoracotomy. Access to the pericardial space is gained via a sub-xiphoid route.

This involves penetrating the chest wall below the xiphoid process.

The sub-xiphoid route has several disadvantages. First, because the pericardial sac which surrounds the heart is a tight-fitting fibrous membrane, the pericardial space is so small that it is difficult to penetrate the sac without also puncturing, and thereby, damaging the heart itself. Second, accessing the heart via the sub-xiphoid route entails a high risk of infection. These are likely to account for its failure to be adopted into common clinical practice.

In fact, the sub-xiphoid route is presently used almost solely for pericardiocentesis, a process for the aspiration of excess fluid from the pericardial sac. Pericardiocentesis is normally performed to treat cardiac tamponade, a build-up of excess fluid in the pericardial sac. The excess fluid distends the pericardial sac away from the heart such that the risk of puncturing the heart is reduced, but the risk of infection remains high.

U.S. Pat. Nos. 4,884,567 to Elliott et al., 4,946,457 to Elliott, and 4,998,975 to Cohen et al. disclose methods for transvenous implantation of electrodes into the pericardial space. A catheter is introduced through a vein to the atrium where the lateral atrial wall is penetrated in order to introduce electrodes into the pericardial space. A major problem encountered by these methods is how to penetrate the lateral atrial wall without also puncturing the tight-fitting pericardium.

The methods of these patents attempt to solve this problem through several elaborate schemes. One scheme involves using complex catheters to attach to the lateral atrial wall and to pull it back away from the pericardium prior to penetrating the wall in order to avoid puncturing the pericardium. Another approach involves injecting a fluid into the pericardial space to distend the pericardium away from the lateral atrial wall prior to penetrating the wall.

U.S. Pat. No. 4,991,578 to Cohen discloses a method for implanting epicardial defibrillation electrodes into the pericardial space. The method involves entering the pericardial space via the sub-xiphoid route. As discussed above, it is difficult to penetrate the pericardial sac via the sub-xiphoid route without also puncturing, and thereby damaging, the heart itself. Like the method discussed directly above, the '578 patent discloses injecting a fluid into the pericardial space or attaching and pulling on a catheter to distend the pericardial sac away from the heart.

Because each of these known methods is intrinsically cumbersome and hazardous, they have not gained widespread use. What is needed is a simpler, safer, and more effective way of accessing the pericardial space for delivery of electricity directly to the heart muscle.

In addition to providing a convenient location for placement of electrodes, the confines of the pericardial sac provide an excellent opportunity to isolate the heart for treatment and diagnosis. By introducing pharmacologic agents directly into the pericardial sac, high cardiac drug concentrations can be achieved without spillage or systemic distribution to other organs or tissues.

The pericardial sac has been used for containment of pharmacologic agents for a number of years in experimental settings, but delivery has heretofore required open chest surgery to access the pericardial space. U.S. Pat. Nos. 4,003,379 and 4,146,029 to Ellinwood disclose an implantable medication dispensing apparatus which is adapted to dispense drugs to the pericardial sac over a long period of time, for example, to prevent arrhythmias. The Ellinwood patents, however, do not teach a method for routing the drugs into the pericardial sac.

U.S. Pat. No. 5,269,326 to Richard L. Verrier discloses a method for transvenously accessing the pericardial space via the right auricle. The full text of the Verrier '326 patent is incorporated herein by reference as if reproduced in full below. The transvenous method described by Verrier overcomes the limitations noted above with prior methods by providing a method for safely and reliably introducing a catheter and/or electrodes into the pericardial space. The present invention improves upon the Verrier '326 patent by providing a specific method for exploiting the route discovered by Verrier.

SUMMARY OF THE INVENTION

A method for placing various types of catheters into the pericardial space takes advantage of the fact that the right auricle is a thin-walled, low-pressure structure which can be readily penetrated without damaging the pericardium or the epicardium. A guide catheter is passed through a selected peripheral vein to establish a transvenous route to the right auricle of the heart. A needle catheter is then passed through the guide catheter and into the right auricle so that a distal end of the needle catheter is positioned against a wall of the right auricle. The wall of the right auricle is then pierced with the needle catheter. A guide wire is advanced through the needle catheter and into the pericardial space. Once in position, the guide wire can be used as a conduit over which a desired catheter may be introduced for performing a specific medical procedure.

To place the guide catheter in position, a peripheral vein such as one of the femoral veins is selected. An introducer sheath is then placed into the selected vein to protect the entry site. The guide catheter is introduced into the vein through the sheath and is guided downstream through the vein to one of the venae cavae, through the one venae cavae to the right atrium, and through the right atrium into the right auricle. If the jugular vein is selected for access, then the superior vena cava is employed as a route to the right atrium.

The guide catheter is advanced into the apex of the right auricle so that a distal end of the guide catheter is placed against the wall of the right auricle. Fluoroscopic imaging can be used to visually follow the progress of the guide catheter into the right auricle. Proper placement of the guide catheter against the wall of the right auricle is confirmed when the distal end of the guide catheter moves with the beating of the heart.

Fluoroscopic imaging can also be used to visually follow the progress of the guide wire into the pericardial space. Proper placement of the guide wire in the pericardial space can be confirmed when the guide wire begins to take the shape of the contour of the heart.

In a preferred embodiment of the invention, the wall of the right auricle is pierced by waiting, once the distal end of the needle catheter is positioned against the wall of the right auricle, for movement of the heart from its rhythmic beating to cause the distal end of the needle catheter to pierce the wall of the right auricle. This method minimizes the chance that the needle catheter will be abruptly pushed into the pericardial space, possibly damaging a coronary vessel or other tissue.

Once the guide wire is in position within the pericardial space, the needle catheter may be removed. Thereafter, any number of different procedure-specific catheters may be introduced to the pericardial space by passing them over the guide wire (i.e., the lumen of the procedure-specific catheter is threaded over the guide wire). Once a specific catheter is positioned within the pericardial space, a medical procedure may be performed on the heart. Such medical procedures include, for example, the delivery of an electrical signal for pacing, cardioverting and/or ablating arrhythmias; the sensing of an electrocardiogram (ECG) signal; the acute or chronic delivery of a pharmacologic agent; the delivery of a dye or imaging agent; the withdrawal of a fluid sample for analysis; and the withdrawal of fluid for treatment of cardiac tamponade. In addition, the guide wire can be used to place a variety of surgical materials or instruments into the pericardial space.

In an alternate embodiment of the invention, once the guide wire is in position, it may not be necessary to guide any other device into the pericardial space. The guide wire itself may be used to remove or introduce a fluid from or into the pericardial space. The guide wire may also act as an electrode for sensing or delivering an electrical signal. The guide wire may also embody a fiber optic device or other instrument.

While the fight auricle has been shown to be an ideal site for entering the pericardial space, the inventors note that the method of the present invention can also be used to access the pericardial space through any other portion of the right atrium.

In another embodiment of the invention the guide catheter includes means for monitoring blood pressure and electrocardiogram. These features permit placement of the guide catheter into position in the right atrium using electrical and/or hemodynamic indices.

An advantage of the invention is that successful placement of the guide wire into the pericardial space can be confirmed without the need to inject a radiopaque dye. In addition, the guide wire maintains a stable point of entry into the pericardial space to permit repeated successive introduction of different intrapericardial catheters.

Another advantage of the invention is that the guide wire permits accurate positioning of an intrapericardial catheter at any location within the pericardial space.

The foregoing and other features and advantages of the invention will be apparent from the following more particular description of a preferred embodiment of the invention, as illustrated in the accompanying drawings.

BRIEF DESCRIPTION OF THE DRAWINGS

FIG. 3 is a flow chart showing the method of the invention for introducing a guide wire into the pericardial space via a transvenous route.

DESCRIPTION OF THE PREFERRED EMBODIMENT

The preferred embodiment of the invention is discussed with reference to the figures in which like reference numbers indicate like elements. Furthermore, the left most digit of each reference number indicates the number of the figure in which the number first appears. While specific part numbers and configurations are discussed, it should be understood that this is done for illustration purposes only. A person skilled in the art will recognize that other components and configurations may be used without departing from the spirit and scope of the invention.

The invention is a method for treating and diagnosing the heart selectively via the pericardial space without surgical trauma or the risks of general anesthesia and infection. Neither thoracic nor sub-xiphoid access is utilized, and there is minimal risk of damage to the pericardium or the epicardium. The method takes advantage of the fact that the pericardial sac isolates the heart such that it may be treated or diagnosed separately from the remainder of the body. Because of its feasibility and safety, this method could lead to common usage by cardiologists and open up the field of pericardial therapy. Heretofore there has been reluctance to pursue this field because of the hazardous and cumbersome nature of existing techniques for accessing the pericardial space.

Figure 1:
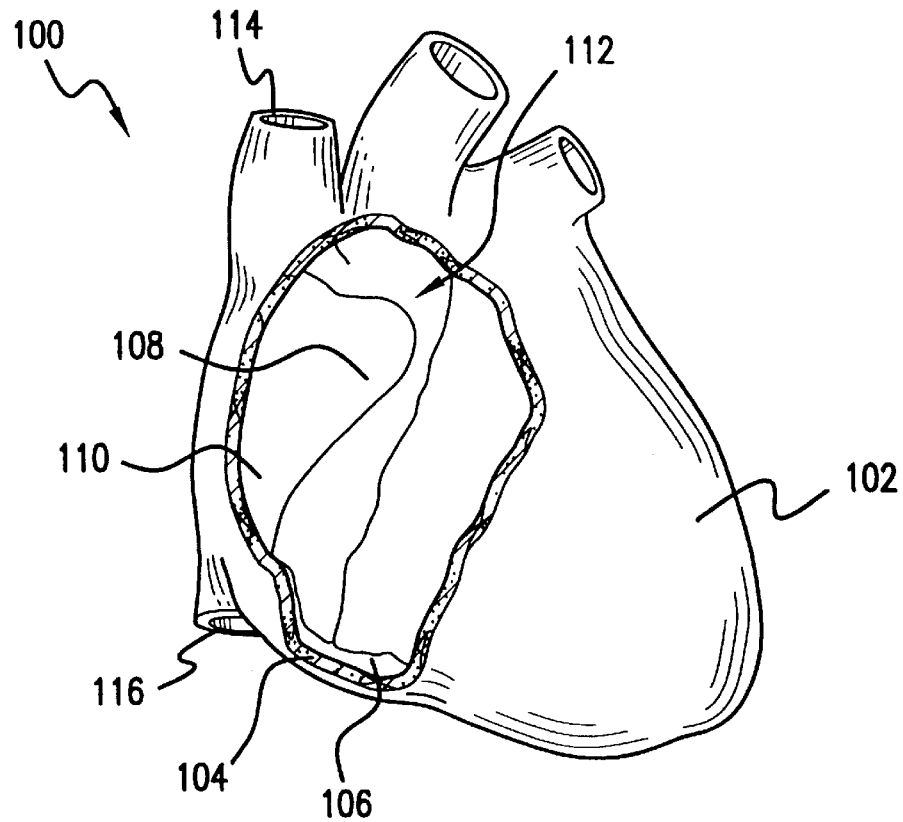
FIG. 1 is a simplified diagram of a human heart with a portion of pericardium 102 cut away.

FIG. 1 shows a heart 100 isolated from the body. Blood is returned to the heart by the superior vena cava 114 and the inferior vena cava 116. The pericardium or pericardial sac 102 encases the cardiac muscle (i.e., epicardium, myocardium and endocardium). A portion of pericardium 102 has been removed to show the underlying cardiac muscle including the right atrium 110. The cut edge of pericardium 102 is designated 104. The small space which is present between the heart muscle and pericardium 102 is known as the pericardial space 106.

In the above referenced U.S. Pat. No. 5,269,326 to Richard L. Verrier, Verrier teaches that the right atrial appendage or right auricle 108 is an ideal site for entry into the pericardial space. Ideally, a transvenously guided catheter can be made to penetrate the thin wall of right auricle 108 at its apex 112. Verrier teaches accessing the right auricle 108 via conventional venae cavae routes. The present invention improves upon the method taught by Verrier in the '326 patent and provides a specific method that can be used to exploit the route discovered by Verrier.

Figure 2:
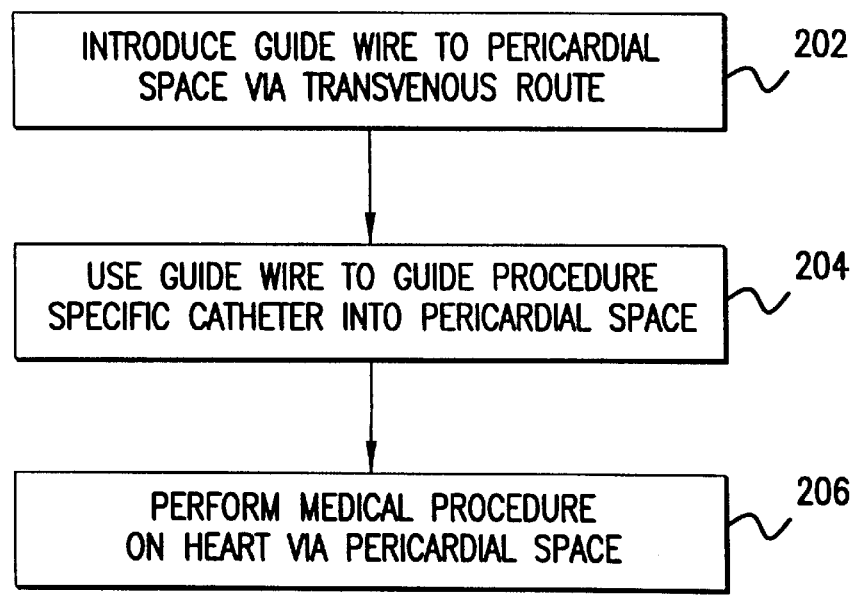
FIG. 2 is a flow chart showing a high level depiction of the present invention.

FIG. 2 is a high level flow chart illustrating the steps of gaining access to the pericardial space to perform a medical procedure. In a step 202, a guide wire is introduced into the pericardial space via a transvenous route. In step 204, the guide wire is used to guide a procedure specific catheter into the pericardial space. This is typically done by threading a catheter with a hollow lumen over the guide wire so that the guide wire passes through the lumen of the catheter as it is maneuvered into position. The procedure specific catheter may be, for example, a catheter specifically configured to sense electrical energy (an electrocardiogram) from the epicardium, to deliver electrical energy to the heart for pacing or ablating or cardioverting arrhythmias, to acutely or chronically deliver a pharmacologic agent to the pericardial space, or to remove fluid from the pericardial space.

Finally, in a step 206, the medical procedure is performed on the heart via the catheter placed in the pericardial space. Any number of procedures may be performed on the heart once the guide wire is in place. In addition, catheters may easily be swapped in and out with little risk to the patient. Thus, an important part of the invention is the method for positioning the guide wire into the pericardial space via the transvenous route.

In the preferred embodiment of the invention, the guide wire is left in place during the medical procedure. Thus, if a different catheter is subsequently required, it may be threaded over the guide wire and into the pericardial space. In an alternate embodiment of the invention, the guide wire may be removed after the procedure specific catheter is put in place. If subsequent introduction of other catheters is desired, the guide wire may be put back into position in the pericardial space by passing it back through the lumen of the procedure specific catheter before the procedure specific catheter is removed.

Figure 4:
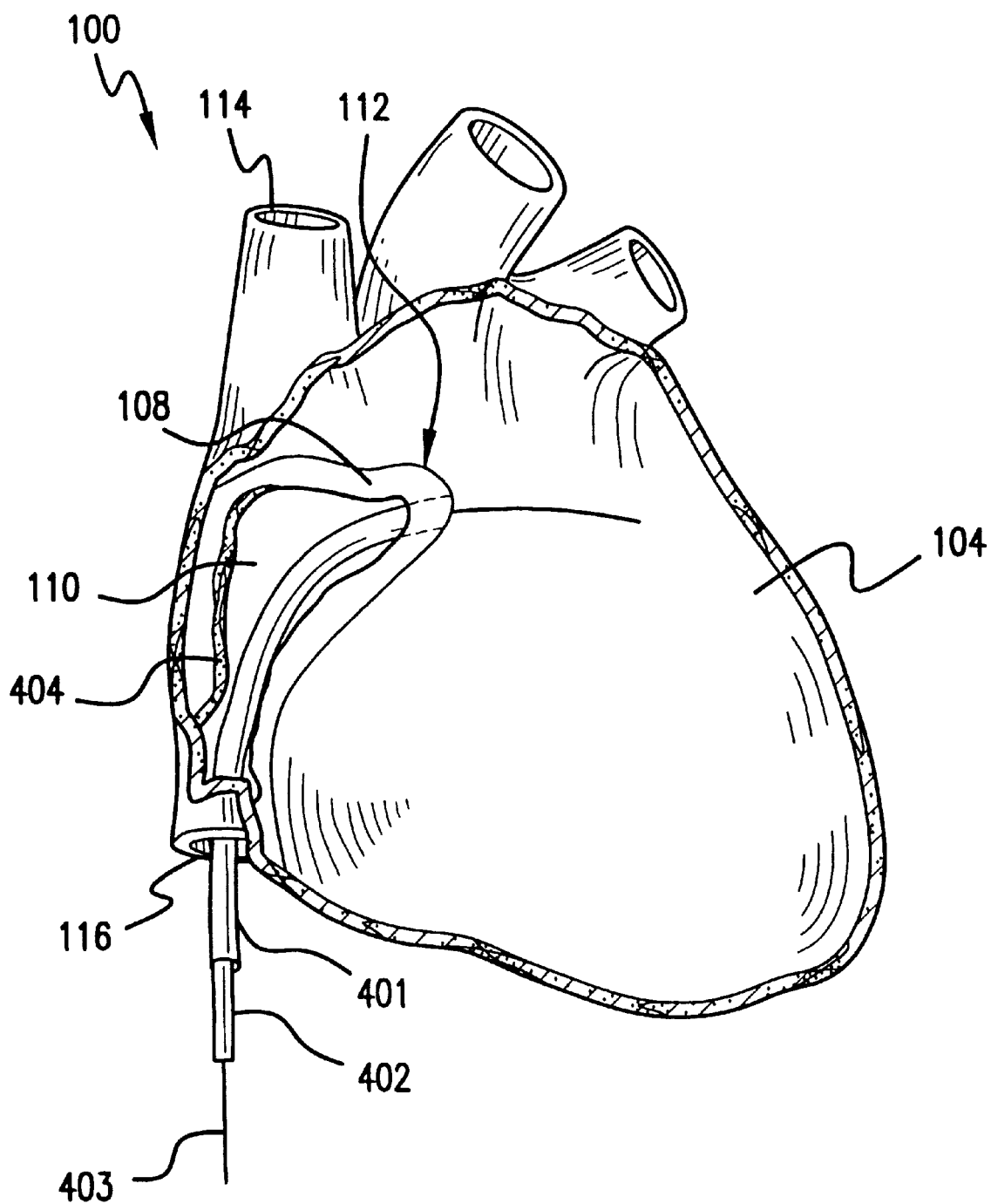
FIG. 4 is a simplified diagram of a human heart as shown in FIG. 1 but with a portion of the right atrium cut away to show the introduction of catheters into the right auricle.

Step 202 of positioning the guide wire in the pericardial space is shown in greater detail with reference to FIGS. 3 and 4. FIG. 3 illustrates the steps of the method. FIG. 4 shows the heart 100 of FIG. 1 with a cutaway 404 to illustrate passage of various catheters 401–403 through inferior vena cava 116, through right atrium 110 and into right auricle 108 as described with reference to FIG. 3.

In a step 302, a peripheral vein is selected as an access site. The Verrier '326 patent teaches a variety of peripheral veins that can be used. For example, if a femoral route is chosen, the great saphenous vein, superficial femoral vein or deep femoral vein can be used. Each of these veins leads downstream to the external iliac vein and finally to the inferior vena cava. If a jugular route is chosen, then access to the right atrium will be made through the superior vena cava.

In a step 304, the access site is prepared by placing an introducer sheath into the vein. The introducer sheath will protect the entry site and facilitate entry into the vein. The sheath is preferably a self-sealing sheath that will prevent bleeding. Such sheaths are commercially available and are commonly used for angioplasty and angiography procedures.

In a step 306, a guide catheter 401 is passed through the introducer sheath, through the peripheral vein, through any downstream veins and into one of the venae cavae. From the selected one of the venae cavae, the catheter is passed into the right atrium and into the right auricle. Using fluoroscopic guidance, the distal tip of guide catheter 401 is placed against the wall of right auricle 108 at apex 112. Proper placement of guide catheter 401 against the wall of the right auricle is then confirmed when the distal end of guide catheter 401 moves with the beating of the heart. In the case of a femoral route, for example, guide catheter 401 may be introduced into one of the femoral veins and then passed through the external iliac vein, through inferior vena cava 116 and into right atrium 110.

A 7 French, multipurpose catheter, available from Cordis Corporation, Miami Lakes, Fla., has typically been employed for guide catheter 401. However, larger or smaller catheters can be selected to accommodate the devices to be introduced therethrough. In an alternate embodiment of the invention, guide catheter 401 may include means for monitoring blood pressure and electrocardiogram. These features permit placement of the guide catheter into position in the right atrium using electrical and/or hemodynamic indices.

In a step 308, a needle catheter 402 is passed through a lumen of guide catheter 401. Needle catheter 402 is advanced through guide catheter 401 until the distal end of needle catheter 402 extends out from the distal end of guide catheter 401. The distal end of needle catheter 402 may then be urged against the wall of right auricle 108 by placing a slight force on the proximal end of needle catheter 402.

In the animal experiments discussed below, the inventors implemented needle catheter 402 by cutting 4 mm from the distal tip of a 23 gauge needle. This 4 mm portion of the 23 gauge needle was then inserted 2 mm into the end of a 3 French transit catheter so that 2 mm of the distal tip of the needle extended out from the distal end of the transit catheter. A snug fit of the needle into the lumen of the transit catheter was achieved. In an alternate embodiment, needle catheter 402 may be implemented using any catheter, needle or wire that has a hollow lumen and can be used to pierce the wall of right auricle 108. For example, needle catheter 108 may be implemented using a long Brockenbrough-type needle, available from U.S. Catheter Instrument Company (USCI), Billerica, Mass.

In a step 310, the distal end of needle catheter 402 is used to pierce the wall of right auricle 108 to gain access to the pericardial space. In the preferred embodiment, this is accomplished by simply holding the distal end of needle catheter 402 in contact with the atrial wall at apex 112. As the heart contracts, the atrial wall will be further urged against the sharp tip of needle catheter 402. After a short period of time has elapsed (e.g., 30 to 60 seconds), needle catheter 402 will pierce through the wall of right auricle 108 as a result of the mechanical motion of the heart while it beats. This method is preferred to any method that involves piercing the wall by simply applying a force to the proximate end of needle catheter 402. Any method that forces needle catheter 402 through the atrial wall by applying a large pushing force may have a higher risk that the catheter may go through the wall and damage other heart tissue or even a coronary vessel within the pericardial space. The inventors believe that the risk of damage to the heart is greatly reduced if the natural movement of the heart is allowed to cause the penetration.

In a step 312, a guide wire 403 is advanced through the lumen of needle catheter 402 and into the pericardial space. As guide wire 403 is being pushed into the pericardial space, fluoroscopic imaging can be used to confirm, as shown in step 314, that guide wire 403 is actually being advanced into the pericardial space as it exits the distal end of needle catheter 402. For example, as guide wire 403 is pushed two to three inches into the pericardial space, it will begin to take the shape of the space that it is being pushed into. When guide wire 403 begins to take the shape of the contour of the heart, the clinician will note this in the fluoroscopic image. In the preferred embodiment, guide wire 403 is a 0.014 inch, Wizdom guide wire, available from Cordis Corporation.

Once guide wire 403 is in position within the pericardial space, the needle catheter may be removed. Thereafter, any number of different procedure-specific catheters (including surgical instruments such as fiber optic imaging devices) may be introduced to the pericardial space by passing them over the guide wire (i.e., the lumen of the procedure-specific catheter is threaded over the guide wire). Once a specific catheter is positioned within the pericardial space, a medical procedure may be performed on the heart. Such medical procedures include, for example, the delivery of an electrical signal for pacing, cardioverting and/or ablating arrhythmias; the sensing of an electrocardiogram (ECG) signal; the acute or chronic delivery of a pharmacologic agent; the delivery of a dye or imaging agent; the withdrawal of a fluid sample for analysis; and the withdrawal of fluid for treatment of cardiac tamponade.

For delivery of electrical energy to the heart or for sensing the electrical activity from the heart, an electrode catheter can be used. Such a catheter may comprise a single electrode or an array of many electrodes. For delivery of a pharmacologic agent (i.e., a drug) to the heart, the distal end of the delivery catheter can be positioned within the pericardial space so that a drug can be directed to a specific location within the myocardium, such as the fat pad near the coronary vessels.

In an alternate embodiment of the invention, once the guide wire is in position, it may not be necessary to guide any other device into the pericardial space. The guide wire itself may be used to remove or introduce small quantities of fluid from or into the pericardial space, or to act as an electrode for sensing or delivering an electrical signal. The guide wire may also embody a fiber optic device or other instrument.

In a preferred implementation of the method of the invention, guide catheter 401 is left in position until any medical procedure is completed. Guide catheter 401 protects the tissue of the veins along the venous route to the heart from damage when one or more catheters are introduced, manipulated and eventually removed from the pericardial space. However, with guide wire 403 in position, guide catheter 401 is not required and may be removed if desired.

The present invention may be used to place a catheter in the heart for both acute and chronic use. For chronic implantations, guide wire 403 may be removed after a desired catheter has been positioned as desired. For example, a drug delivery catheter or a pacing electrode may be left in place for chronic use. Various known methods may be used to secure the drug delivery catheter or electrode at the puncture site in the atrial wall.

In the preferred embodiment of the invention, the apex of the right auricle is pierced to access the pericardial space. The inventors note, however, that the method of the invention may also be used to enter the pericardial space through any other portion of the right atrium.

The inventors have conducted animal experiments to confirm the efficacy of the above-described method. Using six, adult dogs, seventeen attempts were made to position a guide wire into the pericardial space using a femoral vein or a jugular vein for access. All seventeen attempts were successful with no internal bleeding and no complications. In one animal, 65 ml of anticoagulated blood was first introduced into the pericardial space to simulate tamponade. The blood was successfully removed without complication.

Placement of guide catheter 401 into position over the venous route to the right atrium took approximately five minutes. Once guide catheter 401 was in position, placement of guide wire 403 into the pericardial space took approximately three additional minutes. Fluoroscopic imaging was used during catheterization to monitor progress. The results were confirmed by thoracotomy.

Figure 5:
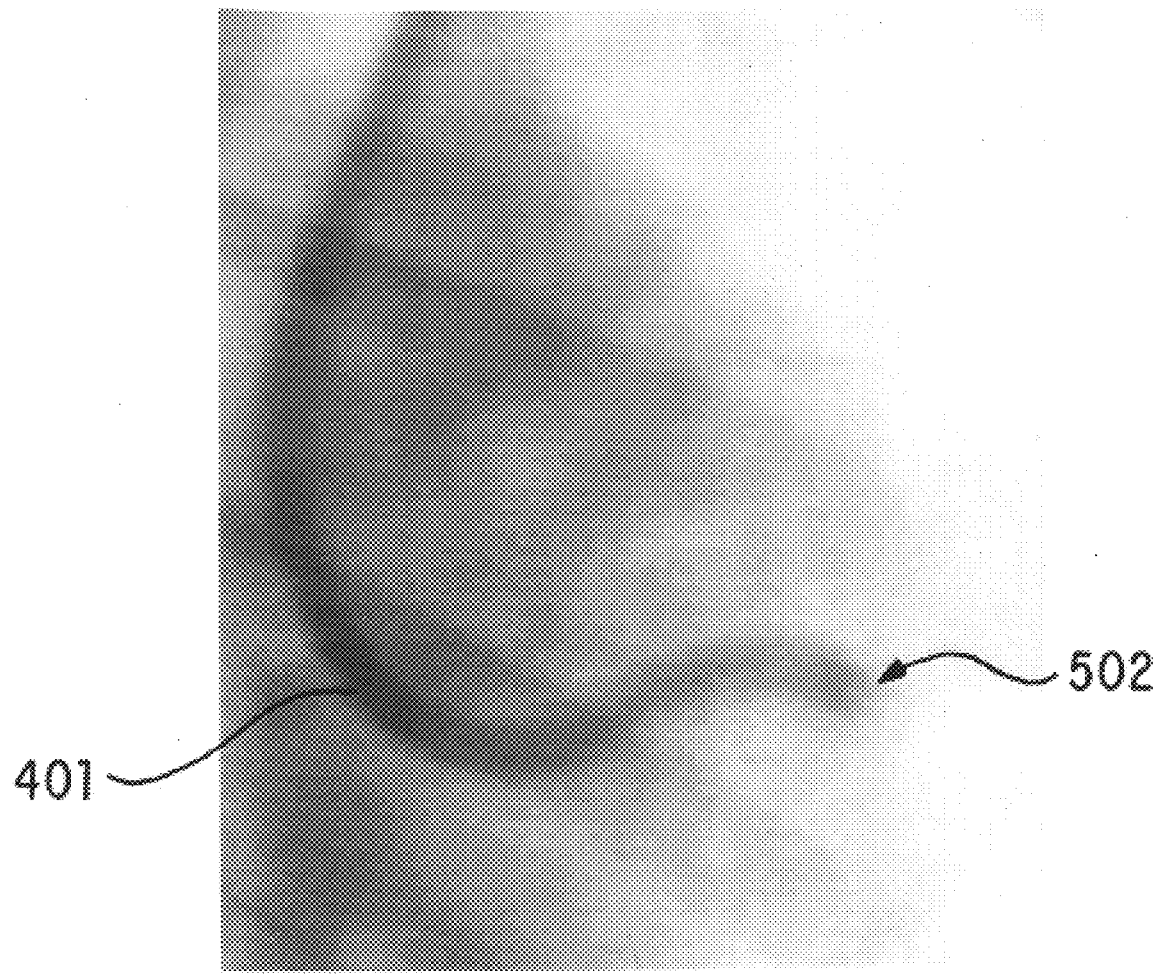
FIG. 5 is a fluoroscopic image showing positioning of a guide catheter into the right auricle.
Figure 6:
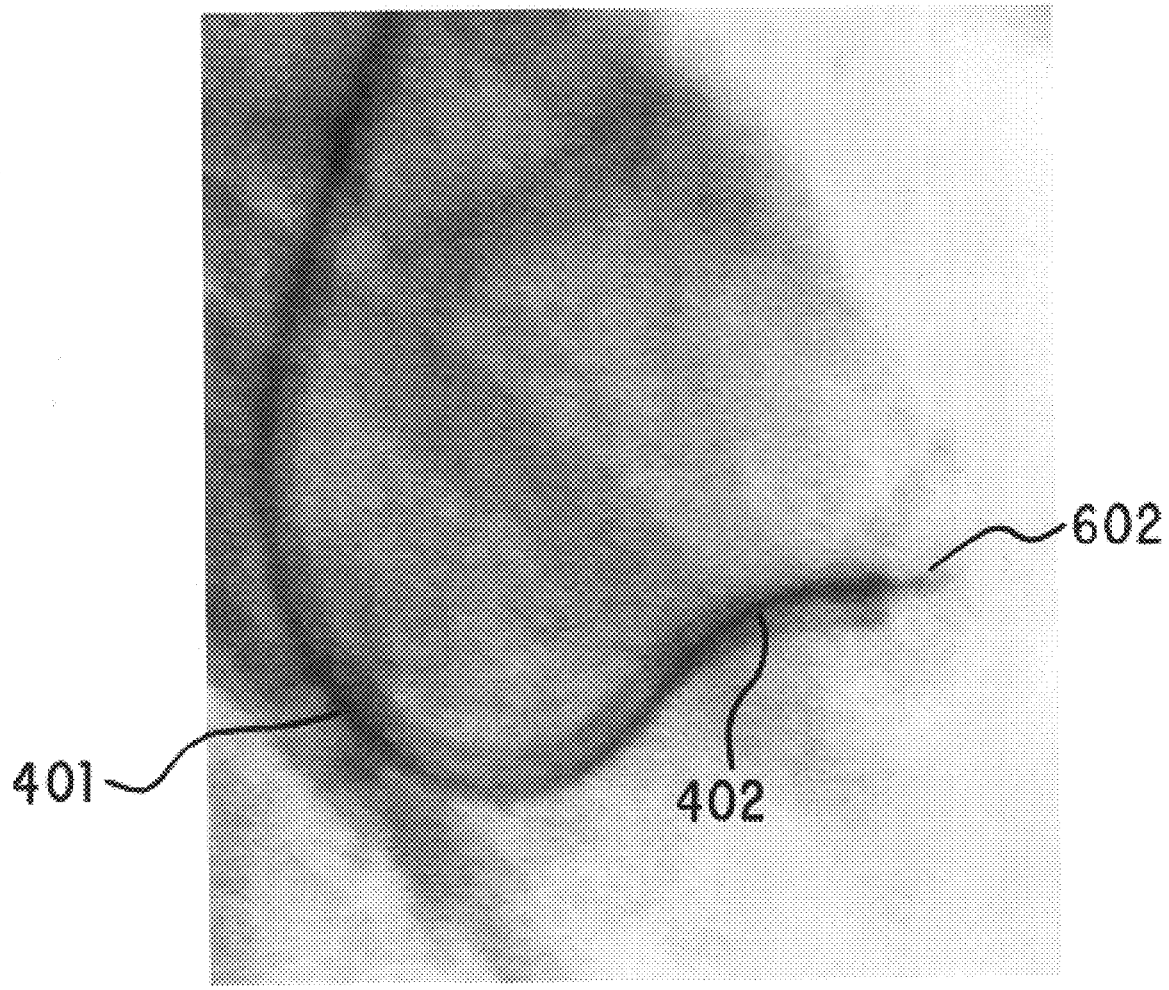
FIG. 6 is a fluoroscopic image showing positioning of a needle catheter through the guide catheter so that a distal tip of the needle catheter is penetrating a wall of the right auricle.

FIGS. 5–8 are fluoroscopic images taken during one of the animal experiments. Referring first to FIG. 5, guide catheter 401 is shown positioned within the right atrium of the heart with a distal tip 502 of catheter 401 positioned closely adjacent to the wall of the right auricle. FIG. 6 is similar to FIG. 5 but, in FIG. 6, needle catheter 402 has been advanced through guide catheter 401 so that a distal tip 602 is extending out from distal tip 502 of guide catheter 401. In this image, distal tip 602 of needle catheter 402 has penetrated the wall of the right auricle.

Figure 7:
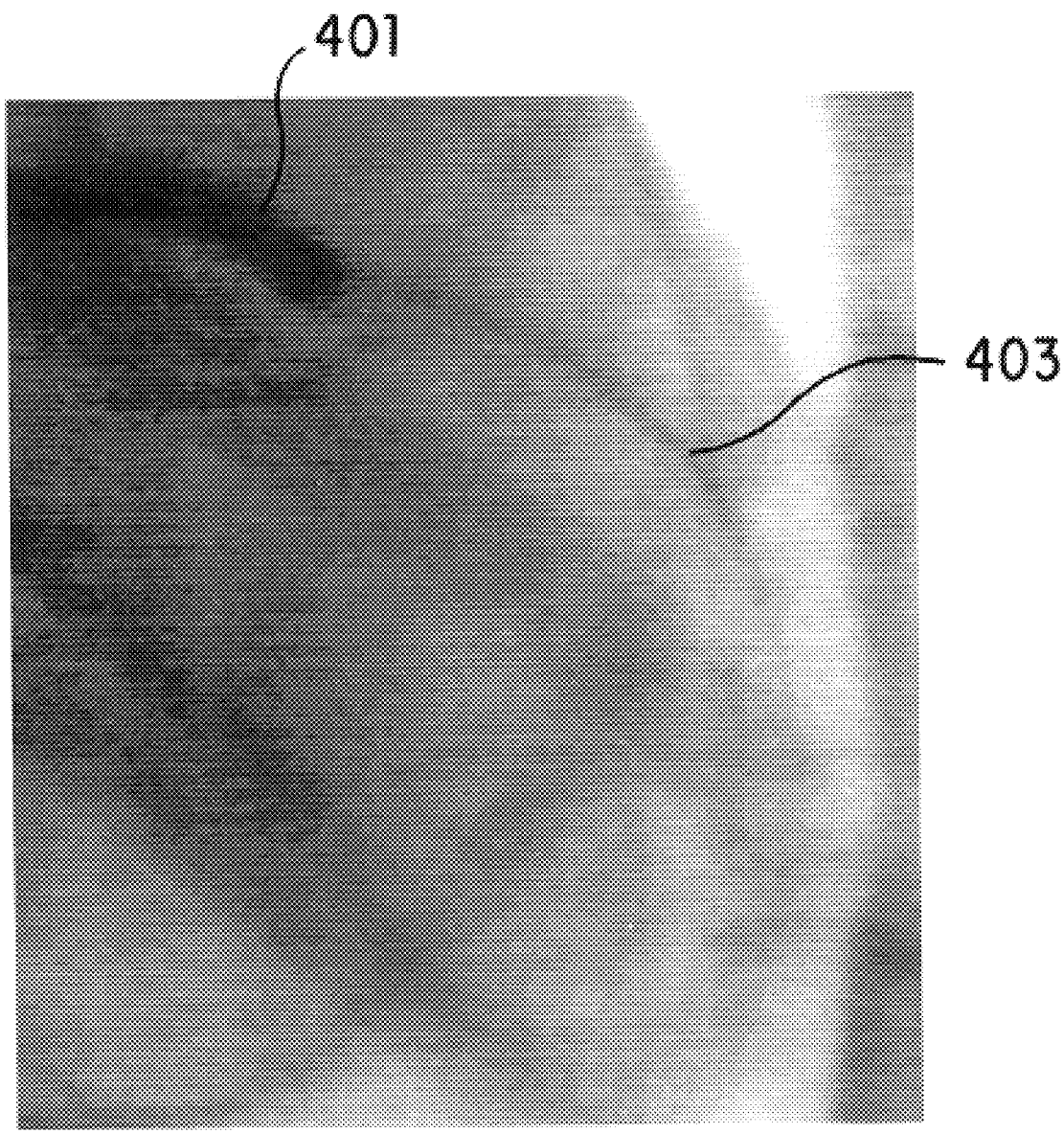
FIG. 7 is a fluoroscopic image showing introduction of a guide wire into the pericardial space through the right auricle.
Figure 8:
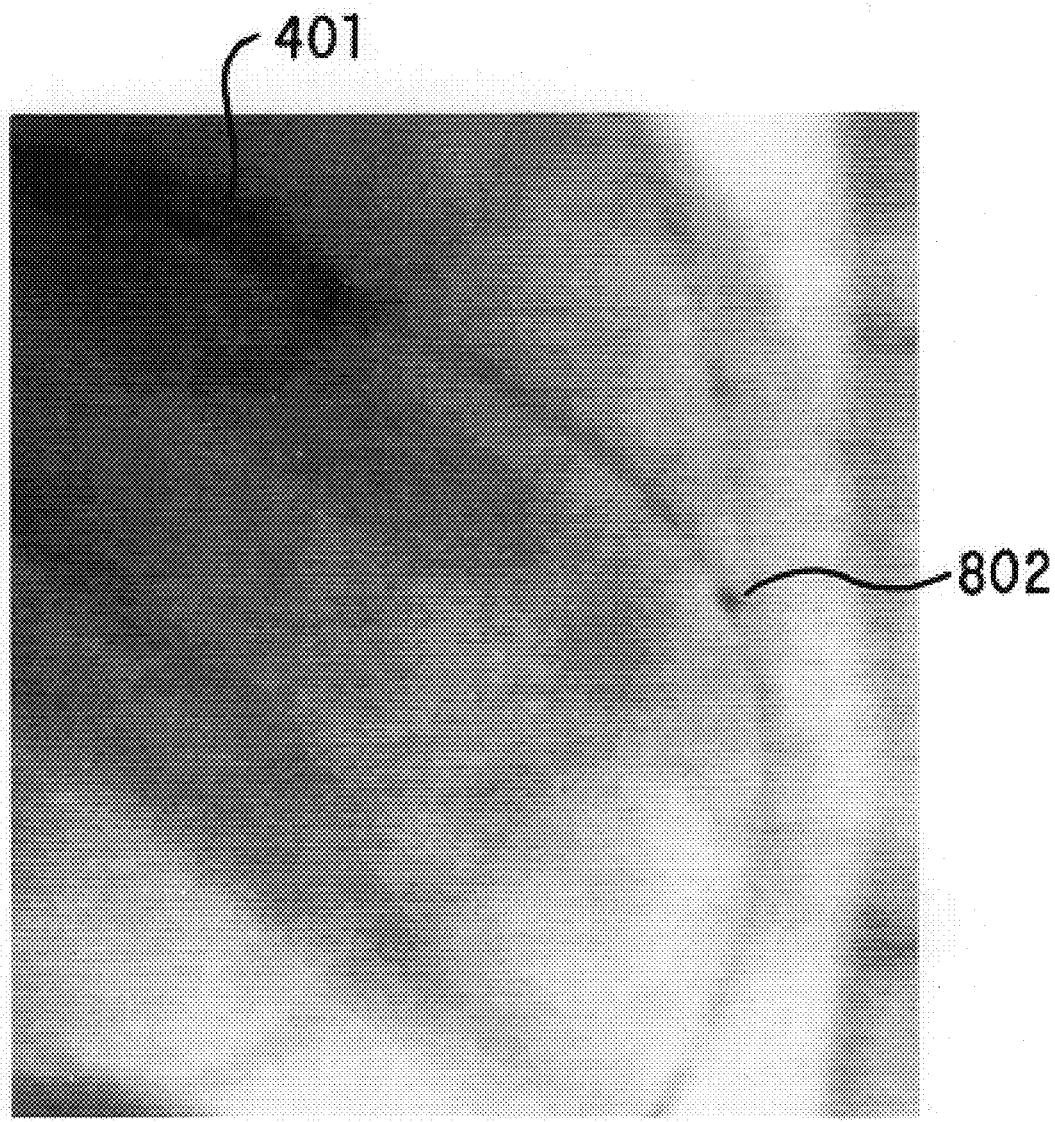
FIG. 8 is a fluoroscopic image showing introduction of an angioplasty catheter over the guide wire and into the pericardial space.

FIG. 7 shows extension of guide wire 403 out from guide catheter 401 and into the pericardial space. Note how guide wire 403 conforms to the shape of the contour of the heart. FIG. 8 is similar to FIG. 7, but in FIG. 8, an angioplasty catheter 801 having a radiopaque marker 802 at its distal tip has been advanced over guide wire 403 and into the pericardial space.

Although the invention has been described and illustrated with a certain degree of particularity, it is understood that those skilled in the art will recognize a variety of applications and appropriate modifications within the spirit of the invention and the scope of the claims.

We claim:

1. A method for transvenously accessing the pericardial space between a heart and its pericardium to perform a medical procedure on the heart, the method comprising the following steps:
    (a) passing a guide catheter through a selected peripheral vein to establish a transvenous route to the right auricle of the heart;
    (b) passing a needle catheter through said guide catheter and into the right auricle so that a distal end of said needle catheter is positioned against a wall of the right auricle;
    (c) piercing said wall of the right auricle with said needle catheter;
    (d) advancing a guide wire through said needle catheter and into the pericardial space; and
    (e) using said guide wire to perform a specific medical procedure on the heart.

2. The method of claim 1, wherein said step (e) of using said guide wire comprises the steps of:
    (e) using said guide wire to perform said specific medical procedure on the heart, said specific medical procedure being selected from the group consisting of (1) withdrawing a fluid from the pericardial space via a lumen of said guide wire, (2) delivering a fluid to the pericardial space via a lumen of said guide wire, (3) using a conductor of said guide wire to deliver an electrical signal to the heart from within said pericardial space, and (4) using a conductor of said guide wire to sense an electrical signal from the heart from within said pericardial space.

3. The method of claim 1, wherein said step (e) of using said guide wire comprises the steps of:

(e) using said guide wire as a conduit over which a desired catheter may be introduced for performing said specific medical procedure.

4. The method of claim 3, wherein said step (e) of using said guide wire further comprises the steps of:

(e) using said guide wire as a conduit over which a desired catheter may be introduced for performing said specific medical procedure, said desired catheter and said specific medical procedure being selected from the group consisting of (1) passing an electrode catheter over said guide wire and into the pericardial space so that a distal end of said electrode catheter is maintained in contact with the epicardium, and using said electrode catheter to deliver electrical energy to said epicardium;

(2) passing an electrode catheter over said guide wire and into the pericardial space so that a distal end of said electrode catheter is maintained in contact with the epicardium, and using said electrode catheter to sense electrical energy from said epicardium;

(3) passing a drug delivery catheter over said guide wire so that a distal end of said drug delivery catheter is positioned in the pericardial space, and using said drug delivery catheter to deliver a pharmacologic agent to the pericardial space; and (4) passing a fluid removal catheter over said guide wire so that a distal end of said fluid removal catheter is positioned in the pericardial space, and using said fluid removal catheter to remove fluid from the pericardial space.

5. The method of claim 1, wherein said step (a) of passing a guide catheter comprises the steps of:

placing an introducer sheath into the selected vein;

introducing a guide catheter into said vein through said sheath;

guiding said guide catheter downstream through said vein to one of the venae cavae;

guiding said guide catheter downstream through said one of the venae cavae to the right atrium; and guiding said guide catheter through the right atrium and into the right auricle.

6. The method of claim 5, wherein said step (a) of passing a guide catheter further comprises the step of:

advancing said guide catheter into the right auricle so that a distal end of said guide catheter is placed against the wall of the right auricle; and using fluoroscopic imaging to visually follow the progress of said guide catheter into the right auricle; and confirming proper placement of said guide catheter against the wall of the right auricle when said distal end of said guide catheter moves with the beating of the heart.

7. The method of claim 6, further comprising the step between steps (d) and (e) of removing said needle catheter.

8. The method of claim 6, wherein said step (c) of piercing comprises the step of:

waiting, once said distal end of said needle catheter is positioned against said wall of the right auricle, for movement of the heart from its rhythmic beating to cause said distal end of said needle catheter to pierce said wall of the right auricle.

9. The method of claim 8, wherein said step (d) of advancing a guide wire further comprises the steps of:

using fluoroscopic imaging to visually follow the progress of said guide wire into the pericardial space; and confirming proper placement of said guide wire in the pericardial space when said guide wire begins to take the shape of the contour of the heart.

10. The method of claim 1, wherein said step (c) of piercing comprises the step of:

waiting, once said distal end of said needle catheter is positioned against said wall of the right auricle, for movement of the heart from its rhythmic beating to cause said distal end of said needle catheter to pierce said wall of the right auricle.

11. The method of claim 10, wherein said step (d) of advancing a guide wire further comprises the steps of:

using fluoroscopic imaging to visually follow the progress of said guide wire into the pericardial space; and confirming proper placement of said guide wire in the pericardial space when said guide wire begins to take the shape of the contour of the heart.

12. A method for transvenously removing fluid from the pericardial space between a heart and its pericardium to treat cardiac tamponade, the method comprising the following steps:

(a) passing a guide catheter through a peripheral vein to establish a transvenous route to the right auricle of the heart;

(b) passing a needle catheter through said guide catheter and into the right auricle so that a distal end of said needle catheter is positioned against a wall of the right auricle;

(c) piercing said wall of the right auricle with said needle catheter;

(d) advancing a guide wire through said needle catheter and into the pericardial space; and (e) removing the fluid from the pericardial space.

13. The method of claim 12, wherein step (e) of removing fluid comprises the step of:

removing the fluid from the pericardial space through a lumen in said guide wire.

14. The method of claim 12, wherein step (e) of removing fluid comprises the step of:

passing a fluid removal catheter over said guide wire so that a distal end of said fluid removal catheter is positioned in the pericardial space; and using said fluid removal catheter to remove pericardial fluid from the pericardial space.

15. A kit for transvenously accessing the pericardial space between a heart and its pericardium to perform a medical procedure on the heart, the kit comprising:

a guide catheter having sufficient length and flexibility to be inserted into the right atrium of a subject's heart via a transvenous route;

a needle catheter having an outer diameter sufficiently small to be passed through a lumen of said guide catheter and having a distal tip capable of penetrating a wall of the said right atrium of the subject's heart, said needle catheter having sufficient length to be passed through said guide catheter and having sufficient flexibility to permit said needle catheter to be passed through said guide catheter into the right atrium of the subject's heart via a transvenous route; and a guide wire having an outer diameter sufficiently small to be passed through a lumen of said needle catheter, said guide wire having sufficient length and flexibility to be passed through said needle catheter and into the pericardial space via a transvenous route and further to permit said guide wire to conform at least partially to the contour of the heart when said guide wire is extended outward from a distal tip of said needle catheter and into the pericardial space.

16. The kit of claim 15, further comprising:

an aspiration catheter having a lumen of sufficient diameter so that said aspiration catheter may be passed over said guide wire and into the pericardial space for the removal of fluid from the pericardial space to treat cardiac tamponade.

17. A method for placing a catheter in the pericardial space between a heart and its pericardium, the method comprising the following steps:

(a) passing a catheter from a selected peripheral vein and through a transvenous route to the right auricle of the heart;

(b) passing said catheter through a wall of the right auricle and into the pericardial space;

(c) monitoring a shape of said catheter as it is advanced into the pericardial space; and (d) confirming proper placement of said catheter in the pericardial space when said shape of said catheter begins to conform to the contour of the heart.

18. The method of claim 17, wherein said catheter comprises:

a guide wire.

19. The method of claim 18, wherein fluoroscopic imaging is used to determine visually when said guide wire begins to take the shape of the contour of the heart.

20. The method of claim 19, further comprising the step of:

(e) using said guide wire as a conduit over which an additional catheter may be introduced for performing a specific medical procedure.

21. A method for placing a catheter in the pericardial space between a heart and its pericardium, the method comprising the following steps:

(a) passing a catheter from a selected peripheral vein and through a transvenous route to the right auricle of the heart;

(b) advancing said catheter so that a distal end of said catheter is placed against the wall of the right auricle; and (c) waiting, once said distal end of said catheter is positioned against the wall of the right auricle, for movement of the heart from its rhythmic beating to cause said distal end of said catheter to pierce the wall of the right auricle.

22. The method of claim 21, wherein said catheter comprises:

a needle catheter.

23. The method of claim 22, wherein said step (b) of advancing said catheter comprises the step of:

confirming proper placement of said catheter against the wall of the right auricle when said distal end of said catheter moves with the beating of the heart.

* * * * *

UNITED STATES PATENT AND TRADEMARK OFFICE
CERTIFICATE OF CORRECTION

PATENT NO. : 5,968,010

DATED : October 19, 1999

INVENTORS : Waxman *et al.*

It is certified that an error appears in the above-identified patent and that said Letters Patent is hereby corrected as shown below.

In item 54 on the cover page, replace "Method" with --Method And Kit--.

In the 'Primary Examiner' listing on the cover page, replace "Mendel" with --Mendez--.

In the 'Attorney, Agent, or Firm' listing on the cover page, replace "Sterne-Kessler-Goldstein & Fox P.L.L.C." with --Sterne, Kessler, Goldstein & Fox P.L.L.C.--.

In the Abstract, line 1, replace "method" with --method and kit--.

In column 1, line 1, replace "Method" with --Method And Kit--.

In column 1, line 8, replace "method" with --method and kit--.

In column 2, line 49, replace "method" with --method and kit--.

In column 4, line 50, replace "method" with --method and kit--.

In column 4, line 55, replace "method" with --method and kit--.

In column 4, line 58, replace "method" with --method and kit--.

Signed and Sealed this

Thirtieth Day of January, 2001

Attest:

Q. TODD DICKINSON

*Attesting Officer*     *Director of Patents and Trademarks*